United States Patent [19]

O'Connor et al.

[11] Patent Number: 5,962,324

[45] Date of Patent: Oct. 5, 1999

[54] THREE DIMENSIONAL OPTIC TISSUE CULTURE AND PROCESS

[75] Inventors: Kim C. O'Connor, New Orleans, La.; Glenn F. Spaulding, Houston, Tex.; Thomas J. Goodwin, Friendswood, Tex.; Laurie A. Aten, Dickinson, Tex.; Karen M. Francis, Aiken, S.C.; Delmar R. Caldwell, Folsom, La.; Tacey L. Prewett, Friendswood; Wendy S. Fitzgerald, Webster, both of Tex.

[73] Assignee: The United States of America as represented by the Administrator of the National Aeronautics and Space Adminstration, Washington, D.C.

[21] Appl. No.: 08/242,546

[22] Filed: May 13, 1994

Related U.S. Application Data

[63] Continuation-in-part of application No. 08/066,292, May 25, 1993, Pat. No. 5,496,722, which is a continuation-in-part of application No. 07/939,791, Sep. 3, 1992, Pat. No. 5,308,764, which is a continuation of application No. 07/317,931, Mar. 2, 1989, Pat. No. 5,153,132, which is a continuation-in-part of application No. 07/317,776, Mar. 2, 1989, Pat. No. 5,155,034, which is a continuation-in-part of application No. 07/213,588, Jun. 30, 1988, Pat. No. 5,235, 161, and a continuation-in-part of application No. 07/213,559, Jun. 30, 1988, Pat. No. 4,988,623, and a continuation-in-part of application No. 07/625,345, Dec. 11, 1990, Pat. No. 5,153,131.

[51] Int. Cl.$^6$ ..................................................... C12N 5/00

[52] U.S. Cl. .......................... 435/394; 435/325; 435/378; 435/379

[58] Field of Search ............................... 435/240.21, 394, 435/325, 378, 379

[56] References Cited

PUBLICATIONS

Eye Bank Association of America, 1993 Statistical Report, EBAA Annual Meeting, Toronto, Canada, Jun. 22–25, 1994.

*Primary Examiner*—Leon B. Lankford, Jr.
*Attorney, Agent, or Firm*—James M. Cate

[57] ABSTRACT

A process for artificially producing three-dimensional optic tissue has been developed. The optic cells are cultured in a bioreactor at low shear conditions. The tissue forms as normal, functional tissue grows with tissue organization and extracellular matrix formation.

22 Claims, 3 Drawing Sheets

(3 of 3 Drawing Sheet(s) Filed in Color)

THREE DIMENSIONAL OPTIC TISSUE CULTURE AND PROCESS

RELATED PATENTS AND APPLICATIONS

The present case is a continuation-in-part of U.S. patent application Ser. No. 08/066,292 filed May 25, 1993, entitled "Process for Complex Three Dimensional Coculture of Normal Human Small Intestine," now U.S. Pat. No. 5,496,722, issued Mar. 5, 1996, which is a continuation-in-part of U.S. patent application Ser. No. 07/939,791, filed Sep. 3, 1992, now U.S. Pat. No. 5,308,764, issued May 13, 1994 entitled "Three-Dimensional Coculture Process" which is a continuing application of Ser. No. 07/317,931, filed Mar. 2, 1989, entitled "Three-Dimensional Coculture Process", now U.S. Pat. No. 5,153,132, issued Oct. 6, 1992, which is a continuation-in-part of Ser. No. 07/317,776, filed Mar. 2, 1989, entitled "Three Dimensional Cell and Tissue Assembly Process", now U.S. Pat. No. 5,155,034, issued Oct. 13, 1992, which is a continuation-in-part of U.S. Ser. No. 07/213,588, filed Jun. 30, 1988, now U.S. Pat. No. 5,235,161, issued Jun. 25, 1991, entitled "Horizontally Rotated Cell Culture System with a Coaxial Tubular Oxygenator" and U.S. Ser. No. 07/213,559, filed Jun. 30, 1988, now U.S. Pat. No. 4,988,623, issued Jan. 29, 1991, entitled "Rotating Bio-Reactor Cell Culture Apparatus", and U.S. Ser. No. 07/625,345, filed Dec. 11, 1990, now U.S. Pat. No. 5,153,131, issued Oct. 6, 1992, entitled "High Aspect Reactor Vessel and Method of Use", all of which are specifically incorporated by reference as if fully set forth herein.

ORIGIN OF THE INVENTION

The jointly made invention described herein was made by employees of the United States Government and may be manufactured and used by or for the Government of the United States of America for governmental purposes without the payment of any royalties thereon or therefor.

The invention described herein was also made by inventors in the performance of work under a NASA contract with Krug Life Sciences and a memorandum of understanding with Tulane University and is subject to the provisions of Section 305 of the National Aeronautics and Space Act of 1958, Public Law 85-568 (72 Stat. 435; 42 U.S.C. 2457).

FIELD OF THE INVENTION

The invention relates to the production of three dimensional tissue from a culture of cells in fluid media.

BACKGROUND OF THE INVENTION

Optic tissue associated with light transmission and image focusing for photoreception is formed in almost all animal life forms. The cornea is exemplary of optic tissue.

In vivo, the cornea serves to focus light and to form the anterior wall of the eye. It is composed of transparent tissue that is on average 0.55 mm thick in the central region of the cornea and 11 mm in diameter in adult humans, and is organized into six distinct regions lying parallel to the anterior and posterior surface. The structural order of these regions gives rise to the transparence of the cornea. The epithelium is located on the anterior surface of the cornea and is composed of five to six layers of cells in humans. The basal layer of the epithelium is connected via numerous attachment bodies to the basement membrane, a tightly packed filamentous layer 100 to 300 Å thick. On the posterior side of this membrane, lies the stroma which accounts for nine-tenths of the thickness of the cornea in most mammals. It is composed primarily of keratocytes and, to a far lesser degree, leucocytes that lie between nearly 200 parallel layers of stroma lamellae that is formed from extracellular matrix. The outermost anterior portion of the stroma forms the Bowman's zone. Approximately 12 $\mu$m thick, this zone is a cell-free layer of stroma containing extracellular matrix fibrils felted together in an irregular manner. The stroma is located between two membranes, the basement membrane as previously discussed and Descemet's membrane which is a sheet of extracellular matrix, 5 to 10 $\mu$m thick, bound to the posterior side of the stroma. This second membrane is lined by the endothelium, a single layer of cells, that forms the posterior surface of the cornea. These cells are characterized by their hexagonal shape, giving the endothelium a mosaic structure. This and other information on corneal tissue is summarized by Kaufman [Kaufman, H. E., McDonald, M. B., Barron, B. A., and Waltman, S. R., The Cornea (Churchill Livingstone, N.Y., 1988)].

Within corneal tissue, the extracellular matrix serves as scaffolding to provide mechanical strength and structural organization. After being synthesized and secreted from corneal cells, the matrix forms distinct three-dimensional, lattice-like arrangements in the extracellular space of corneal tissue [Komai, Y. and Ushiki, T., *Invest. ophthalmol. Vis. Sci.*, 32, 2244 (1991)]. Considering the stroma, fibrils of extracellular matrix are interwoven to form dense felt-like sheets in Bowman's layer. At the interface between the stroma and Descemet's membrane, the matrix becomes a loose fibrillar network oriented in various directions and interlaced. In between these two regions, the stroma is composed of successively stacked layers of flat lamella bundles of matrix fibrils.

There are primarily two classes of macromolecules present in the extracellular matrix: glycosaminoglycans (GAG'S) including chondroitin sulfate and dermatan sulfate, and fibrous proteins such as fibronectin and collagen. The role of the latter group is mainly structural and adhesive. For example, fibronectin binds to cells and to other matrix macromolecules, promoting cell attachment to and subsequent migration along the matrix [Alberts B., Bray, D., Lewis, J., Raff, M., Roberts, K., and Watson, J. D., Molecular Biology of the Cell (Garland Publishing, New York, 1989)]. In the cornea, GAG's regulate spacing between fibrils and the three-dimensional organization of stroma lamellae [Hahn, R. A. and Birk, D. E., Development, 115, 383 (1992)]. In addition, they regulate the kinetics of fibril formation [Birk, D. E. and Lande, M. A., *Biochim, Biophys. Acta*, 670, 362 (1981)].

Expression and proper three-dimensional organization of extracellular matrix is essential for corneal transparency. When expression or organization is inhibited, the tissue becomes opaque. This condition occurs in patients with muscular dystrophy. The disease is characterized by improper biosynthesis of keratin sulfate, a GAG [Hassell, J. R., Newsome, D. A., Krachmer, J. H., and Rodrigues, M., *Proc. Natl. Acad. Sci. U.S.A.*, 77, 3705 (1980); Nakazawa, K., Hassell, J. R., Hascall, V. C., Lohmander, L. S., Newsome, D. A., and Krachmer, J., *J. Biol. Chem.*, 259, 13751 (1984)]. It can also be induced chemically with agents such as β-D xyoside [Hahn, R. A. and Birk, D. E., *Development*, 115, 383 (1992)].

Corneal transplants are the most frequently performed human transplant procedure. Since 1961, there have been more than 421,300 corneal transplantations performed in the U.S. In 1991 alone, there were 41,300 such transplantation, more than all other organ transplantations performed in that year [Eye Bank Association of America, *Annual Report*

(Washington, D.C., 1992]. Greater than 90% of corneal transplant operations successfully restore vision. The reasons for transplantation are varied. They include corneal dystrophy which results from, for example, malnutrition, dehydration and radiation exposure; keratoconus which can cause the cornea to rupture if change in corneal shape is severe; keratitis from viral or microbial sources; corneal degeneration in the elderly; chemical injury; physical trauma; transplant rejection; edema which can result from trauma to the endothelium inhibiting fluid flow between the cornea and anterior chamber; and corneal leukoma [Leibowitz, H. M., *Corneal Disorders: Clinical Diagnosis and Management* (W. B. Saunders, Philadelphia, 1984; Brightbill, F. S., *Corneal Surgery: Theory, Technique, and Tissue* (Mosby-Year Book, St. Louis, 1993)].

The majority of corneal transplantations are performed with donor tissue. The use of donor tissue results in several complications, including donor shortage. There are in excess of 5,000 patients on waiting lists for donor tissue throughout the U.S. [Eye Bank Association of America, *Annual Report* (Washington, D.C., 1992)]. These people wait between two weeks and two years to obtain suitable tissue. And when this tissue becomes available, there is still the possibility of transplant rejection and disease transfer of HIV [Salahuddin, S. Z., Palestine, A. G., Heck, E., Ablashie, D., Luckenbach, M., McCulley, J. P., and Nussenblatt, R. B., *Am. J. Ophthalmol.*, 104, 149 (1986)], hepatitis B [Raber, I. M. and Friedman, H. M., *Am. J. Ophthalmol.*, 104, 255 (1987)], herpes [Leibowitz, H. M., Corneal Disorders: *Clinical Diagnosis and Management* (W. B. Saunders, Philadelphia, 1984], and other ailments from donor to patient. In addition to these complications, many patients with corneal disease or injury are not amenable to transplantation. This can occur, for example, when there is a chemical burn resulting in severe scarring and vascularization [Brightbill, F. S., *Corneal Surgery: Theory, Technique, and Tissue* (Mosby-Year Book, St. Louis, 1993)].

To overcome these difficulties, alternatives to donor tissue have been developed. One such alternative is a prosthetic implant made of an optical cylinder and supporting flange [Polack, F. M. and Heimke, G., *Ophthalmology*, 87, 693 (1980); Trinkaus-Randall, V., Banwatt, R., Capecchi, J., Leibowitz, H. M., and Franzblau, C., *Invest. Ophthalmol. Vis. Sci.*, 32, 3245 (1991)]. For post-operative stability, implant materials must be biocompatible and promote cell adhesion. When these two specifications are met, good vision can be retained for 7 to 8 years after implantation. Permanent stability, however, has yet to be obtained. In refractive keratoplasty procedures, a synthetic intracorneal lens can be implanted to change the refractive power of the cornea [McCarey, B. E., *Refract. Corneal Surg.*, 6, 40 (1990); Insler, M. S., Boutros, G., and Caldwell, D. R., *Am. Intra-Ocular Implant Soc. J.*, 11, 159 (1985)]. As before, biocompatibility and cell adhesion are required for implantation to be successful, but another requirement is permeability so that nutrients can flow across the lens to the anterior portion of the cornea. Synthetic lenses have been stable in animal models for almost a decade. Clinical trials are in an early stage.

The invention described in this patent application is another alternative to the use of donor tissue for transplantation. It can be used to prepare corneal tissue from in vitro cultures of the patient's own corneal cells or from a well-defined primary culture derived from another human source. With in vitro produced tissue, shortage of tissue and disease transfer to the patient would be minimized. Also, post-operative stability should be greatly enhanced with artificially generated tissue over that currently obtained with a prosthesis or synthetic intracorneal lens.

Reported corneal tissue regeneration has been limited to date to two-dimensional models. In particular, regenerated corneal endothelial cells have been successfully transplanted into animal models [Insler, M. S., and Lopez, J. G., *Curr. Eye Res.*, 5, 967 (1986)]. Since the endothelium consists of a single layer of cells in the cornea, a two-dimensional culture can be used for transplantation. Since both the corneal epithelium and stroma are composed of multiple layers of cells, three-dimensional tissue is required to replace these cell structures when they become damaged.

To study cell structure and function in normal and abnormal cornea, three types of tissue models are currently employed: intact tissue in living animals [Trinkaus-Randall, V., Banwatt, R., Capecchi, J., Leibowitz, H. M., and Franzblau, C., *Invest. Ophthalmol. Vis. Sci.*, 32, 3245 (1991)], donor tissue [Komai, Y. and Ushiki, T. *Invest. Ophthalmol. Vis. Sci.*, 32, 2244 (1991)], and tissue from in vitro cell culture [Geroski, D. H. and Hadley, A., *Curr. Eye Res.*, 11, 61 (1992)]. The demand for these models is increasing yearly. The number of donor eyes that were used for research and education grew from 34,147 in 1989 to 40,239 in 1991 [Eye Bank Association of America, *Annual Report* (Washington, D.C., 1992)]. In vitro cell culture has certain advantages over the other two models: its use avoids unnecessary loss of sight in lab animals and avoids variation in tissue characteristic of corneas from different donors. To date, the majority of cell-culture models have been two-dimensional. These models are limited in their applications, however, in that they preclude an accurate representation of three-dimensional phenomena within the cornea such as wound healing and mass transport of nutrients from the endothelium to the stroma and to the epithelium. For these phenomena, a three-dimensional model is required. Furthermore, the synergistic interaction between different cell types in a three-dimensional model could more accurately reflect the cell function in vivo than a two-dimensional model.

The use of conventional stirred or sparged bioreactors have not been generally successful for culture of three dimensional, functional tissue. Some tissues such as the Chinese hamster ovary cells grow robustly in conventional stirred bioreactors [O'Connor, K. C. and Papoutsakis, E. T., *Biotechnol. Tech.*, 6, 323 (1992)]. In contrast Sf9 fall armyworm ovary cells will not grow at all in these reactors under the same operating conditions; in fact, they die unless supplemented with a liquid surfactant [Murhammer, D. W. and Goochee, C. F., *Biotechnol. Prog.*, 6, 391 (1990)]. Only limited work has been done to date to develop three-dimensional corneal models. Bioreactors have not been used for optic tissue growth such as cornea tissue. For example, a model of multiple layers of rabbit corneal epithelial cells grown on a support of contracted collagen lattices was employed to investigate wound healing [Ouyang, P. and Sugrue, S. P., "Identification of an Epithelial Protein Related to the Desmosome and Intermediate Filment Network," *J. Cell Biol.*, Vol. 118, pages 1477–1488, 1992] rather than bioreactor produced cells.

A variety of different cells and tissues, such as bone marrow, skin, liver, pancreas, mucosal epithelium, adenocarcinoma and melanoma, have been grown in culture systems to provide three dimensional growth in the presence of a pre-established stromal support matrix. U.S. Pat. No. 4,963,489, Three-Dimensional Cell and Tissue Culture System, Naughton, et al., Oct. 16, 1990; U.S. Pat. No. 5,032,508, Three-Dimensional Cell and Tissue Culture System, Naughton, et. al., Jul. 16, 1991. A biocompatible, non-living material formed into a three dimensional structure is inoculated with stromal cells. In some cases, the three dimensional structure is a mesh pre-coated with collagen. Stromal cells and the associated connective tissue proteins naturally secreted by the stromal cells attach to and envelop the three dimensional structure. The interstitial spaces of the structure become bridged by the stromal cells, which are grown to at least subconfluence prior to inoculating the three dimensional stromal matrix with tissue-specific cells. The cells are grown on an artificial architecture rather than allowing for establishing natural organization with dimensional segregation.

The invention described herein more closely approximates intact corneal tissue than other in vitro models currently available. In the Sugrue model described above, the contracted collagen lattices serve as a synthetic extracellular matrix to which corneal cells can attached. Because these lattices do not form the intricate structure of the native matrix within corneal tissue, the Sugrue model precludes the formation of cell structures characteristic of native corneal tissue and, thus, precludes the formation of transparent tissue. In the model described in this invention, the internal structure of the tissue is more akin to native cornea. Specifically, the tissue grown on extracellular matrix synthesized by the cells themselves. There is also evidence of special organization of the matrix and cells as well as dimensional segregation in the tissue.

SUMMARY OF THE INVENTION

Aggregates of optic tissue exemplified by cornea tissue have been produced in vitro. The cell aggregates form tissue by three dimensional cell growth. The cells grow and multiply without artificial architecture as shown in prior culture systems. The cells are functional and exhibit the characteristics of normal cells in the three dimensional growth and the formation of extracellular matrix. The extracellular matrix is produced by the functional interrelationship of cell to cell contact. As the artificially produced cell aggregates grow they form their own natural structure, organization and architecture without an artificial structure. The artificial architecture or structure of the prior culture systems, such as collagen lattices, prevent normal three-dimensional tissue formation including extracellular matrix formation. The cell aggregates of the present form the artificial tissue more nearly shown with organized dimensional segregation. The cells differentiate and grow along dimensional boundaries that are characteristic of the normal functional tissue. Differentiation leads to segregation of cell types. Cell function can be confirmed by immunocytochemistry with antibodies specific to particular components produced by the cell types.

The artificially produced optic cell aggregates and tissue were produced under low shear conditions. The low shear conditions are contrasted to stirred or sparged bioreators that attempt to suspend cells in culture media, but produce such forces that cells such as optic cells would die. Low shear is preferably created by using a cylindrical culture vessel that rotates about its central horizontal axis and contains suitable culture media. During culture the horizontal rotation is modulated to create low shear conditions providing the environment for three dimensional cell growth. A cell attachment means is provided in the culture vessel so that there is cell to cell contact sufficient for growth which can be other cells or a microcarrier. The microcarrier may be dissolvable and as the cultured cells grow the microcarrier dissolves completely away leaving only the tissue mass.

The bioreactors preferred for use in this process are referenced and incorporated into this disclosure. In the preferred culture process the vessel is rotated to create low shear at a low speed so that the circular motion of the culture media minimizes centrifugal forces sufficient to move cells outwardly from the rotational axis yet suspends the cells throughout the vessel during culture. The preferred cells are cornea and mammalian optic cells. A further preferred cell inoculum is a mixed population of primary corneal cells containing endothelial cells, epithelial and keratocytes.

DESCRIPTION OF THE DRAWINGS

The file of this patent contains at least one drawing executed in color. Copies of this patent with color drawing (s) will be provided by the Patent and Trademark Office upon request and payment of the necessary fee.

DETAILED DESCRIPTION OF THE INVENTION

Figure 1:
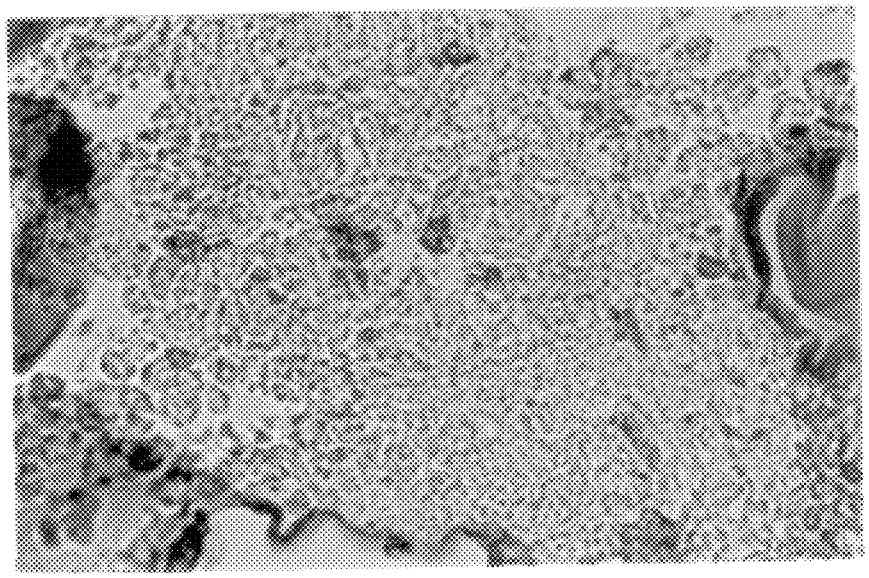
FIG. 1. Negative control of corneal tissue at 200X magnification for the immunocytochemistry study. This control was prepared in the absence of primary antibody. The photograph shows the extensive, multi-layer growth of corneal cells in the HARV after 50 days of cultivation.

Three-dimensional corneal tissue has been produced from an in vitro culture of primary rabbit corneal cells to illustrate the production of optic cells from aggregates and tissue. This tissue is a three-dimensional spheroid that more closely approximates intact corneal tissue in size and in morphology than has yet been achieved in vitro. To generate the tissue, corneal cells were cultured in a bioreactor called the High Aspect Ratio Vessel (HARV) described in the published patent application by the National Aeronautics and Space Administration in the Scientific and Technical Aerospace Reports Volume 29/Number 9, May 8, 1991, ACC NOS. N91-17531, U.S. Ser. No. 625,345, now U.S. Pat. No. 5,153,131, entitled "A Culture Vessel With Large Perfusion Area to Volume Ratio," invented by David A. Wolf, Clarence F. Sams and Ray P. Schwarz and filed on Dec. 11, 1990 and issued October 6, 1992, previously incorporated by reference.

The corneal tissue described herein is unique and the HARV produced tissue has distinctive features. Corneal tissue is one of the most dependent on the formation of three-dimensional extracellular matrices. As discussed herein, these matrices are responsible for the intricate order of cell layers in the cornea and, in turn, are responsible for its transparency and focusing power. This invention demonstrates that these matrices form and provide an internal structure to corneal tissue. This invention demonstrates that the HARV supports robust grown of corneal cultures.

The corneal tissue produced in the HARV was initiated from a mixed population of primary corneal cells (BioWhittaker, Walkersville, Md) containing endothelial cells, epithelial cells and keratocytes. These cells are attachment dependent and, as such, were grown bound to a support, Cytodex-3 microcarrier beads (Pharmacia, Piscataway, N.J.). To prepare the beads for culture, they were first hydrated in $Ca^{2+}$, $Mg^{2+}$free phosphate buffer saline (PBS) for 3 hours with occasional gentle agitation at room temperature and a concentration of 50–100 ml/g bead. The beads were subsequently washed with fresh (30–50 ml/g bead) and sterilized at 115° C. and 15 psi for 15 minutes in PBS at the same concentration. Before initiating a microcarrier culture, the PBS was washed from the sterile beads by rinsing in ward culture medium.

Alternative attachment means may be used such as dissolvable microcarriers. Also other cells introduced into the culture may be an attachment means so that the cells use each other as support.

Corneal cultures were grown in two types of vessels: the HARV and a Bellco spinner flask (Vineland, N.J.). The latter vessel served as a control with which to compare the HARV. The spinner flask is the conventional vessel of choice for the preparation of the microcarrier cell cultures. In both vessels, cultures were inoculated with $1\times10^5$ viable cells/ml and a bead density of 5 mg/ml in 50 ml GTSF-2 medium (NASA, Houston, Tex.) containing 5% (v/v) fetal bovine serum. During cultivation, the vessels were maintained at pH 7.4, 37° C., 5% $CO_2$ and 95% relative humidity. Corneal cells were fed according to glucose consumption, maintaining a level of 40–80 mg/dl glucose.

Prior to inoculation, spinner flasks were siliconized with Sigmacote (Sigma, St. Louis, Mo.) to prevent cell adhesion to the flask walls. Corneal cells were maintained in suspension in the spinner flask by impeller mixing at 60 rpm. These cultures reached stationary phase within one week of inoculation. At that time, cells had attached to the microcarrier beads, but there was minimal aggregation of beads. As a result, no tissue formed in the shaker flask.

Figure 3:
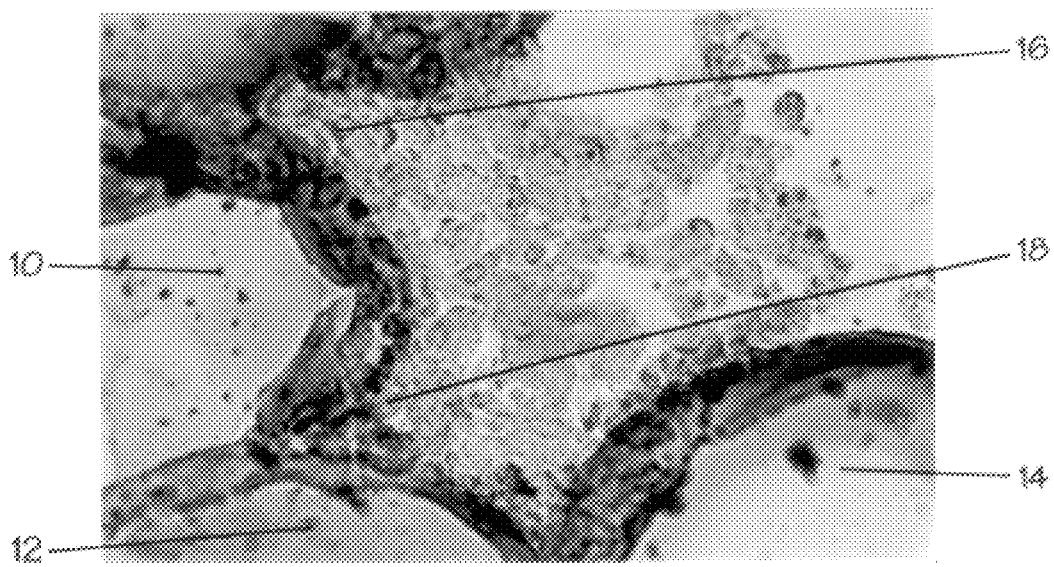
FIG. 3. Cell-bead aggregates at 200X magnification in which corneal cells have bridged between microcarrier beads. The tissue has stained strongly positive for chondroitin-4-sulfate.

For HARV cultivation, cells were suspended in culture medium by end-over-end rotation of the vessel at 11–25 rpm. The vessel was completely filled with medium, eliminating cell damage from hydrodynamic forces associated with air/liquid interfaces and boundary layer at the vessel wall. The HARV has three ports for medium replacement and sampling. Replacing medium in HARV required stopping vessel rotation, allowing the cells to settle, and removing 20% of the spent medium through the top port. Fresh medium was then injected under sterile conditions with a syringe. Within 24 hours of inoculation, cells attached to the microcarrier beads. After an additional week, cell/bead aggregates developed as cells bridged between beads as shown in FIG. 3. These aggregates grew in size to form tissue in the HARV over 2.5 months.

The concentration of cells present in either vessel was measured by counting released nuclei. Specifically, aggregated corneal tissue was exposed to 25 µg/ml collagenase type IA (Sigma) in $Ca^{2+}$, $Mg^{2+}$-free PBS containing 0.02% (w/v) ethylenediaminetetraacetic acid at 37° C. to release cell nuclei. Next, the nuclei were stained with 0.1% (w/v) crystal violet in 0.1 M citric acid (Sigma) and counted with a hemocytometer.

The tissue produced in the HARV from corneal cells is a three-dimensional spheroid greater than 5 mm in diameter containing multiple layers of cells as shown in FIG. 1. The maximum cell density that was achieved in the HARV was in excess of $1\times10^7$ cells/ml. In contrast, the corneal cells grew for only a period of a week in the spinner flask, reaching a maximum cell density of only $4.5\times10^5$ cells/ml. As mentioned above, aggregation in the spinner flask, reaching a maximum cell density of only $4.5\times10^5$ cells/ml. As mentioned above, aggregation in the spinner flask was not substantial; on average, aggregates were 1 mm in diameter or less. Spinner flasks maintain cells in suspension through impeller mixing. This design generates turbulent eddies in the grown medium which cause cell-cell collisions that disrupt aggregates, inhibiting three-dimensional cell growth [Cherry, R. S. and Papoutsakis, E. T. *Bioprocess Eng.*, 1, 29 (1986)].

Immunocytochemistry was used to characterize the composition and internal organization of artificially produced corneal tissue. For this analysis, tissue samples, each 1.0 ml in volume, were removed from the HARV after 50 days of cultivation. They were washed with PBS and then fixed in 1.0 ml of OmniFix II (An-Con Genetics, Melville, N.Y.), an alcohol-based fixative not containing aldehydes or mercury. Samples were paraffin embedded, blocked, sectioned and mounted on slides using standard methodology. After the mounted sections were deparaffinized and rehydrated, they were exposed to a primary mouse antibody directed against specific proteins expressed in the tissue as shown below in Table 1. This was followed by exposure to a secondary antibody, peroxidase-labeled, anti-mouse antibody (Boehringer Mannheim, Indianapolis, Ind.), which binds to the primary antibody. To visualize antibody binding, sections were incubated with diaminobenzidine (Sigma) solubilized in a solution of Tris buffer and $H_2O_2$. Diaminobenzidine reacts with peroxidase to form a brown color.

TABLE 1

PRIMARY ANTIBODIES USED FOR IMMUNOCYTOCHEMICAL ANALYSIS

| Antibody Specificity | Dilution | Source, Location & Order No. |
| --- | --- | --- |
| Vimentin | 1:20 | Boehringer Mannheim, Indianapolis, IN 1112457 |
| Chondroitin-4-Sulfate | 1:75 | Chemicon, Temecula, CA MAB2030 |
| Chondroitin-6-Sulfate | 1:50 | Chemicon, MAB2035 |
| Fibronectin | 1:40 | Boehringer Mannheim, 1087720 |

Analysis by immunocytochemistry revealed substantial extracellular matrix expression in the corneal tissue. Of the two classes of macromolecules that constitute the matrix, glycosaminoglycans' (GAG's) and fibrous proteins, both were present in the tissue.

Figure 4:
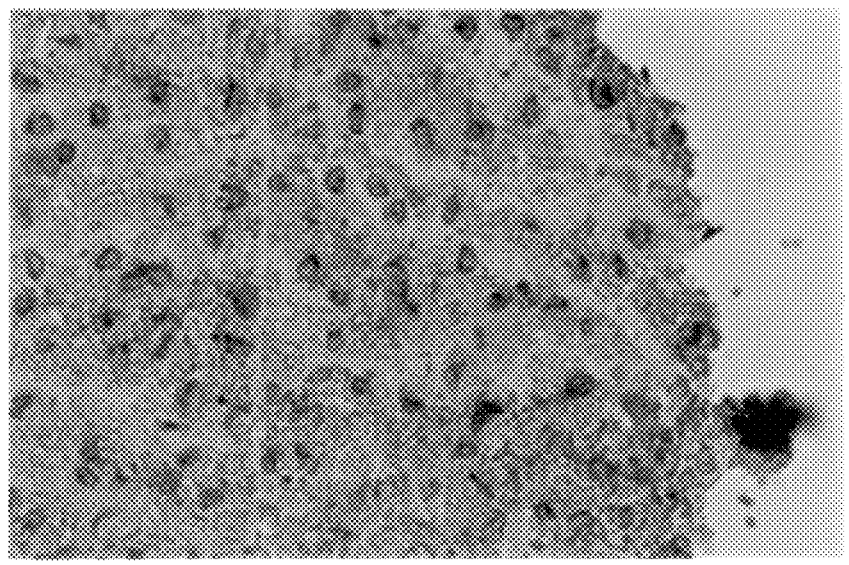
FIG. 4. Corneal tissue at 200X magnification that has stained positive for chondroitin-6-sulfate. Staining demonstrates that chondroitin has organized into layers that are fairly parallel to each other.

The brown color in FIGS. 3 and 4 relative to the negative control in FIG. 1 shows expression of the GAG's chondroitin-4- and -6- sulfate. These two macromolecules are sulfated disaccharides that differ from each other in the position of their sulfate residue. Chondroitin-4-sulfate is sulfated at the C4 position of N-acetyl-D galactosamine, while chondroitin-6-sulfate is sulfated at the C6 position. In FIG. 3, stained for chondroitin-4-sulfate, the microcarrier beads are shown at 10, 12 and 14. The tissue between the beads, for example at 16 and 18, shows the strong staining for matrix component chondroitin-4-sulfate. In FIG. 4, stained for chondroitin-6-sulfate, the tissue shows layers of cells with organized dimensional segregation. The layers of cells appear as waves of cells with staining.

Figure 5:
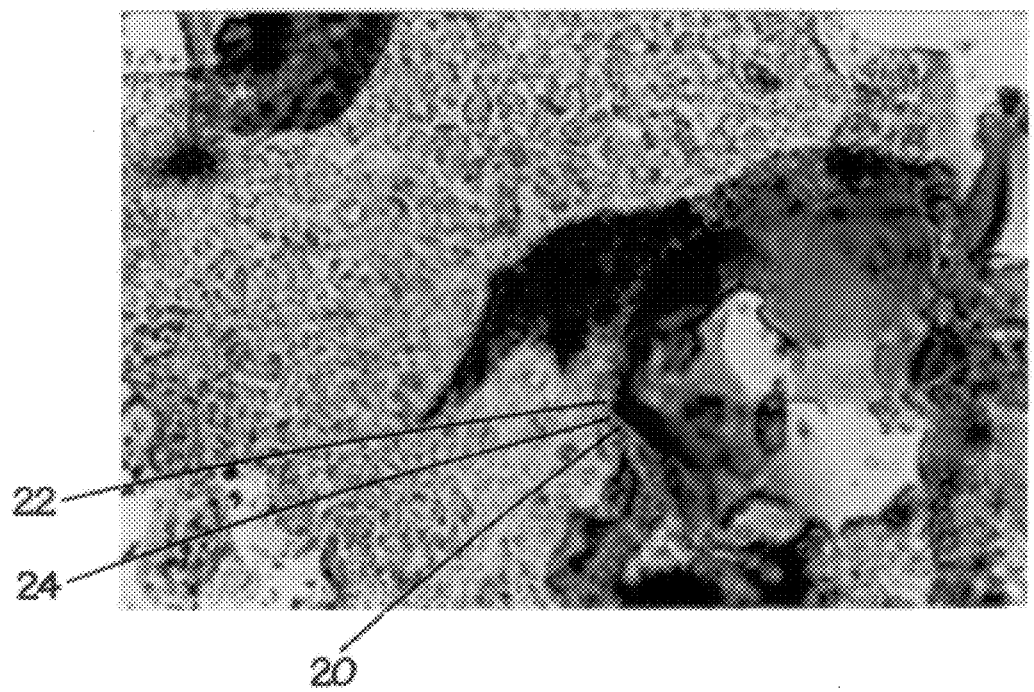
FIG. 5. Tissue growth around a microcarrier bead at 200X magnification. The cells have stained strongly positive for fibronectin at the bead surface and more moderately throughout the tissue.

As for fibrous proteins, fibronectin staining is depicted in FIG. 5. The darker stain as illustrated at reference numerals 20 and 22 is at the bead surface 24. This concentration of fibronectin at the cell bead interface is evidence of matrix organization and promotes cell adhesion to the bead surface.

These figures also reveal three-dimensional organization and segregation of these matrix macromolecules within the artificially produced tissue. In particular, FIG. 4 demonstrates that chondroitin-6-sulfate organized into parallel layers that were separated from each other by 10 $\mu$m on average. While FIG. 5 indicates that fibronectin was moderately expressed through the corneal tissue, it also shows that this protein concentrated at the cell/bead interface to promote cell adhesion to the bead surface.

Figure 2:
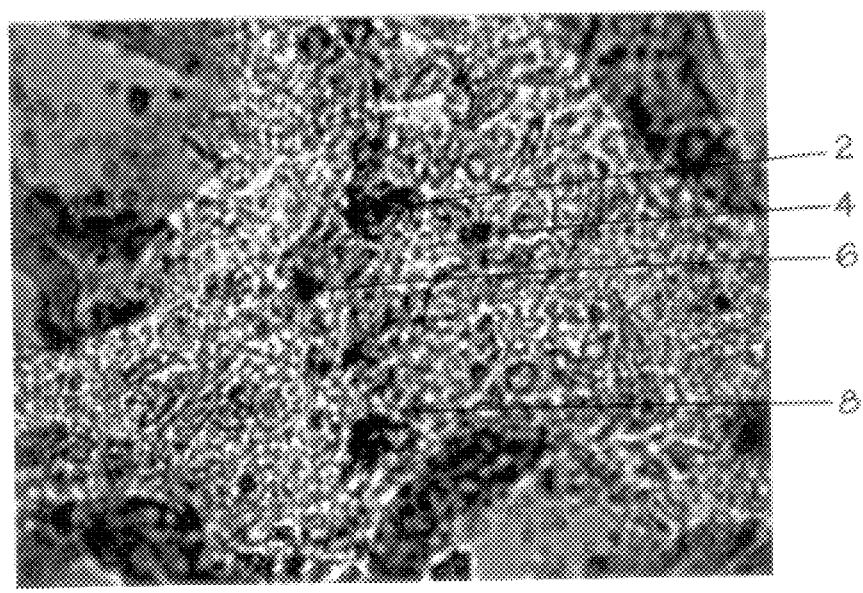
FIG. 2. Immunocytochemical characterization of corneal tissue at 200X magnification. The intense brown color relative to the negative control in FIG. 1 indicates that the tissue has stained strongly positive for vimentin, a protein that is present in keratocytes (a type of fibroblast) and endothelial cells.

Matrix formation permitted cell types within the regenerated tissue to organize and segregate. The cells migrated along the matrix to form distinct clusters of individual cell types. This is evident in FIG. 2. Recall that tissue was prepared from a mixed population of endothelial cells, epithelial cells and keratocytes. FIG. 2 shows strong positive staining for vimentin. This protein is an intermediate filament present in keratocytes and endothelial cells. The dense foci of brown color as shown at reference numerals 2, 4, 6, 8 and elsewhere in the figure depict distinct clusters that these cell types form in vivo. This shows that the cells have organized within the tissue.

The invention of three-dimensional corneal tissue, produced from in vitro cell culture and described herein, is closer in size and in morphology to intact corneal tissue than earlier attempts at in vitro production. This novel three-dimensional tissue can be used to model cell structure and function in normal and abnormal cornea. Also, it can eventually be used to develop tissue for patients requiring corneal transplantations. This process may also be used for non-mammalian optic and cornea tissue production for study and use with other animal forms.

The description of the process and embodiment is illustrative of the invention and is not intended to place any limitation on the claims of invention. Those skilled in the art will recognize other modes of practicing the invention described herein.

What we claim is:

1. A process for producing aggregates of optic cells comprising the steps of:
   (a) selecting the optic cells for culture;
   (b) introducing the cells and a cell attachment means and a culture media into a cylindrical culture vessel that rotates about its central horizontal axis; and
   (c) culturing the cells in the vessel during horizontal rotation modulated to create low shear conditions whereby extra-cellular, optic tissue matrixes are formed and three dimensional cell growth is achieved.

2. A process for producing aggregates of optic cells of claim 1 wherein the culturing process provides for functional interrelationship by cell to cell contact producing the formation of three-dimensional extracellular matrices.

3. A process for producing aggregates of optic cells of claim 1 wherein the cell aggregates are organized with dimensional segregation.

4. A process for producing aggregates of optic cells of claim 1 wherein the vessel is rotated to create low shear at a low speed so that the circular motion of the culture media minimizes centrifugal forces sufficient to move cells outwardly from the rotational axis yet suspends the cells throughout the vessel during culturing.

5. A process for producing aggregates of optic cells of claim 1 wherein the cells are cornea cells.

6. A process for producing aggregates of optic cells of claim 1 wherein the cells are mammalian cells.

7. A process for producing aggregates of optic cells of claim 1 wherein the cells in step (a) are a mixed population of primary corneal cells containing endothelial cells, epithelial cells and keratocytes.

8. A process for producing aggregates of optic cells of claim 1 wherein the cell attachment means in step (d) is selected from the group consisting of cells, microcarriers, and dissolvable microcarriers.

9. A process for producing aggregates of optic cells of claim 1 wherein the three dimensional tissue growth is defined as positive by immunocytochemical staining for chondroitin sulfate.

10. A process for producing aggregates of optic cells of claim 1 wherein the three dimensional tissue growth is defined as positive by immunocytochemical staining for vimentin.

11. A process for producing aggregates of optic cells of claim 1 wherein the three dimensional tissue growth is defined as positive by immunocytochemical staining for fibronectin.

12. An artificially produced optic tissue made by the steps of:
   (a) selecting optic cells for culture;
   (b) introducing the cells and a cell attachment means and a culture media into a cylindrical culture vessel that rotates about its central horizontal axis; and
   (c) culturing the cells in the vessel during horizontal rotation modulated to create low shear conditions whereby extra cellular matrixes are formed and three dimensional tissue growth is achieved.

13. The artificially produced optic tissue of claim 12 with three dimensional extracellular matrices.

14. The artificially produced optic tissue of claim 12 with cells organized with dimensional segregation.

15. The artificially produced optic tissue of claim 12 wherein step (c) the vessel is rotated to create low shear at a low speed so that the circular motion of the culture media minimizes centrifugal forces sufficient to move cells outwardly from the rotational axis yet suspends the cells throughout the vessel during culturing.

16. The artificially produced optic tissue of claim 12 wherein the cells are cornea cells.

17. The artificially produced optic tissue of claim 12 wherein the cells are mammalian cells.

18. The artificially produced optic tissue of claim 12 wherein the cells in step (a) are a mixed population of primary corneal cells containing endothelial cells, epithelial cells and keratocytes.

19. The artificially produced optic tissue of claim 12 wherein the cell attachment means in step (d) is selected from the group consisting of cells, microcarriers, and dissolvable microcarriers.

20. The artificially produced optic tissue of claim 12 wherein the tissue produced is defined as positive by immunocytochemical staining for chondroitin sulfate.

21. The artificially produced optic tissue of claim 12 wherein the tissue produced is defined as positive by immunocytochemical staining for vimentin.

22. The artificially produced optic tissue of claim 12 wherein the tissue produced is defined as positive by immunocytochemical staining for fibronectin.

* * * * *